US010406274B1

(12) United States Patent
Ramirez (10) Patent No.: US 10,406,274 B1
(45) Date of Patent: Sep. 10, 2019

(54) ACCESSING ASSEMBLY FOR HEMODIALYSIS ADMINISTRATION

(71) Applicant: Jose Ramirez, Miami, FL (US)

(72) Inventor: Jose Ramirez, Miami, FL (US)

( * ) Notice: Subject to any disclaimer, the term of this patent is extended or adjusted under 35 U.S.C. 154(b) by 218 days.

(21) Appl. No.: 15/612,186

(22) Filed: Jun. 2, 2017

(51) Int. Cl.
  *A61M 1/36* (2006.01)
  *A61M 25/00* (2006.01)
  *A61M 25/04* (2006.01)

(52) U.S. Cl.
  CPC ........ *A61M 1/3661* (2014.02); *A61M 25/003* (2013.01); *A61M 25/0017* (2013.01); *A61M 25/0041* (2013.01); *A61M 25/04* (2013.01); *A61M 2025/0031* (2013.01); *A61M 2025/0034* (2013.01)

(58) Field of Classification Search
  CPC .............. A61M 1/3653; A61M 1/3661; A61M 2025/0025; A61M 2025/0031; A61M 2025/0035; A61M 2025/0039; A61M 2025/0079; A61M 2039/0258; A61M 2039/0261; A61M 2039/0264; A61M 2039/027; A61M 2039/0276; A61M 2039/0282; A61M 25/0075; A61M 25/04; A61M 39/0247; A61M 39/285; A61M 25/0017; A61M 25/003; A61M 25/0041; A61M 2025/0034
  See application file for complete search history.

(56) References Cited

U.S. PATENT DOCUMENTS

| | | | |
|---|---|---|---|
| 4,762,517 A | 8/1988 | McIntyre et al. | |
| 4,778,452 A | 10/1988 | Moden et al. | |
| 5,026,344 A | 6/1991 | Dijkstra et al. | |
| 5,527,278 A | 6/1996 | Ensminger et al. | |
| 5,628,784 A | 5/1997 | Strecker | |
| 5,848,989 A | 12/1998 | Villani | |
| 6,053,901 A | 4/2000 | Finch, Jr. et al. | |
| 6,398,764 B1 | 6/2002 | Finch, Jr. et al. | |
| 6,582,409 B1 | 6/2003 | Squitieri | |
| 7,261,705 B2 | 8/2007 | Edoga et al. | |
| 7,632,263 B2 | 12/2009 | Denoth et al. | |
| 7,699,821 B2 | 4/2010 | Nowak | |
| 7,803,143 B2 | 9/2010 | Tallarida et al. | |
| 7,828,781 B2 | 11/2010 | Edoga et al. | |

(Continued)

*Primary Examiner* — Brandy S Lee
(74) *Attorney, Agent, or Firm* — Albert Bordas, P.A.

(57) ABSTRACT

An accessing assembly for hemodialysis administration, having an intravascular tube assembly, a conduit assembly, first and second catheter sleeve assemblies, and first and second catheter assemblies. The intravascular tube assembly has an intravascular tube, a subcutaneous cuff, a tube end and a ring with a hole. The conduit assembly has first and second conduits having respective conduit threading. The first and second catheter sleeve assemblies have collapsible sidewalls, ends, and joining ends respectively. The collapsible sidewalls define cavities respectively, and couplers are defined within the cavities. The first and second catheter assemblies have catheter sidewalls, inlet/outlet ends, internal ends, and fasteners respectively. The catheter sidewalls have a plurality of holes. The intravascular tube is implanted within a vascular structure. The catheter sidewalls are positioned inside to respective collapsible sidewalls. The collapsible sidewalls are collapsed until respective fasteners are threaded onto respective couplers.

16 Claims, 6 Drawing Sheets

(56) References Cited

U.S. PATENT DOCUMENTS

| | | | |
|---|---|---|---|
| 7,850,666 B2 | 12/2010 | Schon et al. | |
| 8,079,990 B2 | 12/2011 | Powley et al. | |
| 8,182,453 B2 | 5/2012 | Eliasen | |
| 8,262,629 B2 | 9/2012 | Oster et al. | |
| 8,337,464 B2 | 12/2012 | Young et al. | |
| 8,377,014 B2 | 2/2013 | Ricol | |
| 8,398,577 B2 | 3/2013 | Burnett | |
| RE44,639 E | 12/2013 | Squitieri | |
| 8,608,728 B2 | 12/2013 | Michels et al. | |
| 8,708,979 B2 | 4/2014 | Honaryar et al. | |
| 8,852,160 B2 | 10/2014 | Schweikert et al. | |
| 8,852,217 B2 | 10/2014 | Woodruff et al. | |
| 8,858,514 B2 | 10/2014 | Sarradon | |
| 8,876,788 B2 | 11/2014 | Glenn | |
| 8,882,728 B2 | 11/2014 | Harders et al. | |
| 8,926,573 B2 | 1/2015 | Smith et al. | |
| 8,932,271 B2 | 1/2015 | Hamatake et al. | |
| 8,974,422 B2 | 3/2015 | Gill et al. | |
| 9,033,931 B2 | 5/2015 | Young et al. | |
| 9,174,037 B2 * | 11/2015 | Schutz | A61M 39/0247 |
| 9,295,809 B2 | 3/2016 | Sheetz | |
| 9,415,187 B2 | 8/2016 | Agnew | |
| 2011/0125129 A1 * | 5/2011 | Saab | A61M 39/0247 604/500 |

* cited by examiner

ACCESSING ASSEMBLY FOR HEMODIALYSIS ADMINISTRATION

BACKGROUND OF THE INVENTION

1. Field of the Invention

The present invention relates to medical devices, and more particularly, to accessing assemblies for hemodialysis.

2. Description of the Related Art

Applicant believes that one of the closest references corresponds to U.S. Pat. No. 4,762,517 issued to McIntyre, et al. on Aug. 9, 1988 for Subcutaneously-implanted drug delivery system for intravenous injections, and the like. However, it differs from the present invention because McIntyre, et al. teach a subcutaneously-implanted infusion device that has a portal defining an inner reservoir chamber that allows communication between a septum and an end of a catheter tube connected to the portal. The septum is mounted in a compressed state within a main housing of the portal by a pressure-insert element that is formed against the septum by an arbor press. The septum is then held in its compressed state via a retaining ring cooperating with an annular groove provided in the interior surface of the main housing directly adjacent the lower end of the portal. The device also includes a lower suture-attaching cuff having a skirt portion, with a low profile angle, which is provided with a plurality of separate, spaced-apart, suture-reinforcing tabs. The pressure-insert element is provided with a through-hole for the passage of a catheter with an enlarged abutment stop at one end for preventing passage of the catheter through the through-hole. Medical glue is used to bond the end of the catheter to the interior surface of the pressure-insert element. A protective metal sleeve is mounted about the portion of the catheter directly adjacent the outer circumference of the pressure-insert element for protecting against accidental puncture of the portion of the catheter which extends from the through-hole.

Applicant believes that another reference corresponds to U.S. Pat. No. 4,778,452 issued to Moden, et al. on Oct. 18, 1988 for Implantable infusion port. However, it differs from the present invention because Moden, et al. teach an implantable infusion port for dispensing medication in the body of a patient having a septum which is preferably integrally molded from a nontoxic, rubberized material and has an interior cavity formed therein for receiving medication in the septum, and a catheter element which extends from the cavity to the exterior of the septum for dispensing medication in the body of a patient. The septum has a rounded dome-shaped configuration, and the infusion port is surgically implantable in the body of a patient so that it is positioned beneath the skin and subcutaneous tissue of the patient. After the infusion port has been implanted in the patient, medication can be introduced into the cavity by inserting a hypodermic needle through the skin of the patient and through the sidewall of the septum. The rounded dome-shaped configuration and the integrally molded construction of the septum minimize patient discomfort and provide an increased needle penetration area in the infusion port so that it does not become damaged by needle penetrations and it can be used over a prolonged period of time without requiring replacement.

Applicant believes that another reference corresponds to U.S. Pat. No. 5,026,344 issued to Dijkstra, et al. on Jun. 25, 1991 for Implantable injection chamber device. However, it differs from the present invention because Dijkstra, et al. teach an implantable injection chamber device comprising a housing which encloses an injection chamber and has at least one wall that can be pierced with a hollow needle, and a bore provided in a wall of the chamber, there being further provided connecting means for connecting a catheter to the bore, and in which the connecting means comprise a tube of pliable material which is connected to the bore and in operation extends through a bore in a first member of the connecting means, at least a part of the first member surrounding the tube relatively tightly and the part being provided with a plurality of radially disposed longitudinal grooves; and a second member of the connecting means, which in operation surrounds the part of the first member with longitudinal grooves and is capable of pressing inwardly the parts of the first member between the longitudinal grooves.

Applicant believes that another reference corresponds to U.S. Pat. No. 5,527,278 issued to Ensminger, et al. on Jun. 18, 1996 for Implantable access devices. However, it differs from the present invention because Ensminger, et al. teach an access port for implantation within the body of a patient for providing repeated access to a specific site within the patient and communicating with the site by an implanted internal catheter. The access ports include a housing having an inlet orifice leading to a reduced diameter guide passageway. An external filament such as a needle, guide wire, optical fiber, or external catheter can be introduced into the access device and fed through the housing. The system allows the introduction of therapeutic agents, the removal of fluids from the body, or the introduction of sensing or articulating devices to the specific site within the patient.

Applicant believes that another reference corresponds to U.S. Pat. No. 5,628,784 issued to Ernst P. Strecker on May 13, 1997 for Endoprosthesis that can be percutaneously implanted in the body of a patient. However, it differs from the present invention because Strecker teaches an endoprosthesis that can be percutaneously implanted by means of a catheter in a patient's body, especially inside a blood vessel or other body cavity. The endoprosthesis is oblong and hollow. It can be expanded once properly implanted to fit the lumen of the vessel or cavity. It comprises a sleeve surrounding at least the outside of a skeleton. The sleeve and the skeleton are initially narrow enough to be implanted and expand once they have been implanted. Room is left between the outer surface of the sleeve of the implanted endoprosthesis and the inner surface of the vessel or cavity it is implanted in. Drugs or other substances can be delivered to the room through at least one length of flexible tubing communicating with the sleeve. The sleeve can have spacers projecting radially out of it. The sleeve can also be a hollow membrane with the flexible tubing communicating with it. The sleeve is wrapped around the skeleton, leaving wrinkles and folds.

Applicant believes that another reference corresponds to U.S. Pat. No. 5,848,989 issued to Giuseppe Villani on Dec. 15, 1998 for Implantable port with low profile housing for delivery/collection of fluids and implantation method. However, it differs from the present invention because Villani teaches an implantable port having a low profile housing for delivery/collection of fluids into and out of a body. The low profile housing includes a selectively configured open flared end, which serves to guide a needle directly into an inlet defined in the housing. A septum is mounted in the port's inlet via a hollow core, which is inserted into the housing in a compression fit. The septum is selectively compressed to reduce its deflection characteristic to minimize backflow of fluid into the port. A catheter of selected size may be connected to a port outlet to direct fluid to a desired location. The implant may be configured to have multiple ports or to have a specially adapted outlet for cranial mounting. An implantation method is also provided where only the leading flared end of the port is sutured to the fascia. Where the port is implanted in a laboratory animal, preferably dissolvable sutures are used to permit migration of the port to accommodate the animal's growth.

Applicant believes that another reference corresponds to U.S. Pat. No. 6,053,901 issued to Finch Jr., et al. on Apr. 25, 2000 for Subcutaneously implanted cannula and method for arterial access. However, it differs from the present invention because Finch Jr., et al. teach a catheter with valve for implantation in a vascular structure of a living being. The catheter is in the general shape of a "T" with the top of the "T" implanted within the lumen of a vascular structure, and the leg of the "T" extending out of the vascular structure through an incision in the vascular structure. The lumen of the implanted portion of the catheter completely occupies the lumen of the vascular structure, causing all blood flow through the vascular structure to be directed through the implanted portion of the catheter. A valve is placed in the wall of the implanted portion of the catheter, which opens into the lumen of the leg of the "T" of the catheter upon application of sufficient differential pressure between the lumens of the two portions of the catheter. The leg of the "T" is connected to the sidewall of the implant portion of the catheter at an angle, such that the axis of the lumen of the leg of the "T" intersects the axis of the lumen of the implanted portion of the catheter at approximately a 45-degree angle.

Applicant believes that another reference corresponds to U.S. Pat. No. 6,398,764 issued to Finch Jr., et al. on Jun. 4, 2002 for Subcutaneously implanted cannula and method for arterial access. However, it differs from the present invention because Finch Jr., et al. teach a catheter with valve for implantation in a vascular structure of a living being. The catheter is in the general shape of a "T" with the top of the "T" implanted within the lumen of a vascular structure, and the leg of the "T" extending out of the vascular structure through an incision in the vascular structure. The lumen of the implanted portion of the catheter completely occupies the lumen of the vascular structure, causing all blood flow through the vascular structure to be directed through the implanted portion of the catheter. A valve is placed in the wall of the implanted portion of the catheter, which opens into the lumen of the leg of the "T" of the catheter upon application of sufficient differential pressure between the lumens of the two portions of the catheter. The leg of the "T" is connected to the sidewall of the implant portion of the catheter at an angle, such that the axis of the lumen of the leg of the "T" intersects the axis of the lumen of the implanted portion of the catheter at approximately a 45-degree angle.

Applicant believes that another reference corresponds to U.S. Pat. No. 6,582,409 issued to Rafael Squitieri on Jun. 24, 2003 for Hemodialysis and vascular access systems. However, it differs from the present invention because Squitieri teaches a hemodialysis and vascular access system which includes a catheter having an arteriovenous fistula utilizing an indwelling silastic venous end and an arterial end which is adapted to be anastomosed to an artery is described. The catheter includes a needle receiving through which a needle is inserted to access fluid flow within the hemodialysis and vascular access system. It is also use an "arterialized" indwelling venous catheter where blood flows from an artery through the hemodialysis and vascular access system and is returned to the venous system via an arrangement wherein the outflow opening is distinct and distant from the site where the catheter enters the vein. The site of blood return to the venous system is not directly fixed to the venous wall but is free floating within the venous system. This system provides a hemodialysis and venous access graft.

Applicant believes that another reference corresponds to U.S. Pat. No. 7,261,705 issued to Edoga, et al. on Aug. 28, 2007 for Implantable dialysis access port. However, it differs from the present invention because Edoga, et al. teach an implantable access port which comprises a hollow port casing having a first channel, a second channel and a third channel. A self-sealing insert may be disposed within the third channel. The implantable access port may further comprise a graft having a first branch, a second branch, and a third branch, the first branch extending from the first channel and adapted to be anastomosed to a vessel at a first location, the second branch extending from the second channel and adapted to be anastomosed to a vessel in a second location, the third branch extending at least partially into the third channel, wherein the third branch is disposed between the self-sealing insert and the hollow port casing.

Applicant believes that another reference corresponds to U.S. Pat. No. 7,632,263 issued to Denoth, et al. on Dec. 15, 2009 for Connecting device for percutaneously implanted port system. However, it differs from the present invention because Denoth, et al. teach a port system including an implantable first fluid guiding system, an external second fluid guiding system with a connecting head at one end, a percutaneously implantable port for establishing a fluid connection between the fluid guiding systems, the port including a port casing which forms a first connecting element, and a connecting device which includes a second connecting element, wherein the connecting head is fastened to the port casing by a releasable, engagement of the connecting elements, several embodiments of which connecting elements are encompassed.

Applicant believes that another reference corresponds to U.S. Pat. No. 7,699,821 issued to Piotr Nowak on Apr. 20, 2010 for Multi-functional port. However, it differs from the present invention because Nowak teaches a subcutaneous port including an elongated port corpus having a proximal end defining a septum receiving opening angled in relation to a longitudinal axis of said port corpus, a substantially cylindrical body, and a substantially frustoconical conus having an outlet opening provided at a distal end thereof. The cylindrical body defines a chamber along at least a portion of a length thereof and the cylindrical body and frustoconical conus collectively define a passage to permit passage of fluid between the chamber and the outlet opening. A septum is retained in the septum receiving opening by a septum retainer. A catheter is connected to the port corpus passage.

Applicant believes that another reference corresponds to U.S. Pat. No. 7,803,143 issued to Tallarida, et al. on Sep. 28, 2010 for Implantable hemodialysis access device. However, it differs from the present invention because Tallarida, et al. teach a implantable hemodialysis port including a housing and a septum, the housing being formed from a flexible material and including a plurality of chambers. The chambers are fluidly interconnected with one another by integrated outlet passageways. Each of the chambers includes a sidewall portion and a funnel portion tapering from the sidewall portion. The septum encloses each of the chambers.

Applicant believes that another reference corresponds to U.S. Pat. No. 7,828,781 issued to Edoga, et al. on Nov. 9, 2010 for Implantable dialysis access port. However, it differs from the present invention because Edoga, et al. teach an implantable access post having a port casing core with an aperture therethrough, a patch associated with the port casing core, the patch adapted to be sewn to a vessel to connect the port casing core to the vessel to permit fluid communication from the vessel through the aperture of the port casing core, and an insert disposed within the aperture of the port casing core, the insert adapted to prevent fluid flow through the aperture. The insert may be self-sealing and may include a valve. The port may also include a port outer casing at least partially surrounding the port casing core and further including an anti-vessel-compression mechanism.

Applicant believes that another reference corresponds to U.S. Pat. No. 7,850,666 issued to Schon, et al. on Dec. 14, 2010 for Catheter infusion port. However, it differs from the present invention because Schon, et al. teach a port for a catheter assembly, including a body and a cover and having a distal discharge port for connection to an implanted catheter assembly. Within the body is a longitudinal U-shaped channel extending to a proximal body wall from the distal body wall along a longitudinal axis parallel to the axis of the discharge port. The channel has a rounded bottom and is also rounded at the channel ends at the distal and proximal body walls. The cover provides for penetration by a syringe needle and seals upon needle withdrawal, with the cover having an inside surface concave and rounded between the distal and proximal ends and also longitudinally, being generally smoothed into the channel sides and ends. The port has no inner sharp edges or corners and eliminates blood clotting and unwanted growth sites.

Applicant believes that another reference corresponds to U.S. Pat. No. 8,079,990 issued to Powley, et al. on Dec. 20, 2011 for Implantable catheter port. However, it differs from the present invention because Powley, et al. teach a single or multi-port vascular access device including one or more reservoirs each covered by a needle-penetrable, self-sealing septum. The one or more reservoirs each open to an outlet in a stem to which the catheter is attached. The reservoir may be generally circular or ellipsoid in shape and large enough so that fluid movement into and out of the needle is unimpeded. The fluid passage leading from the reservoir through the outlet into the catheter is defined by unique tapered and tangential geometries in order to maximize flow between the reservoir and catheter and to minimize any regions of impeded or low fluid flow where coagulation or cell shearing may occur. For example, the outlet surface may be globally tangent along the entire reservoir surface, or may be globally tangent along only one side of the reservoir surface.

Applicant believes that another reference corresponds to U.S. Pat. No. 8,182,453 issued to Kenneth Arden Eliasen on May 22, 2012 for Volume reducing reservoir insert for an infusion port. However, it differs from the present invention because Eliasen teaches an access portal including a housing, a body defining a fluid reservoir, and a septum enclosing the fluid reservoir. A stem in fluid communication with the fluid reservoir extends from the fluid reservoir. The access portal also includes a reservoir insert disposed within the fluid reservoir, in which the reservoir insert decreases the fluid fill volume of the reservoir.

Applicant believes that another reference corresponds to U.S. Pat. No. 8,262,629 issued to Oster, et al. on Sep. 11, 2012 for Catheter port. However, it differs from the present invention because Oster, et al. teach a catheter port for supplying an active substance to an active site which is distant from the port. The housing of the port is designed to have two parts, an upper housing part and a lower housing part. The upper housing part holds an insertion part in a clamping manner in a housing recess of the lower housing part, wherein a chamber is arranged in the insertion part for receiving the active substance with the interpositioning of a punctured membrane that can be pierced with an injection cannula. While the insertion part and the chamber can be manufactured from a material resistant to the active substance, preferably a heavier ceramics, the upper and lower housing parts may consist of a lighter biocompatible plastic material. It is advantageous that the patient only comes into contact with the upper and lower housing parts made of a biocompatible plastic material and not with the insertion part.

Applicant believes that another reference corresponds to U.S. Pat. No. 8,337,464 issued to Young, et al. on Dec. 25, 2012 for Vascular access ports and related methods. However, it differs from the present invention because Young, et al. teach ports for accessing vessels within a patient including passageways that can guide needles or other access devices directly into the vessels. The ports can be implanted subcutaneously within a patient. Some ports may be used in the creation and use of vascular access buttonholes.

Applicant believes that another reference corresponds to U.S. Pat. No. 8,377,014 issued to Jean-Paul Ricol on Feb. 19, 2013 for Implantable site with a casing having multiple perforations. However, it differs from the present invention because Ricol teaches an implantable medical device for injecting and/or collecting fluid substance into and/or from a human or animal organism, comprising a casing whose wall delimits a chamber and is pierced with at least a first access orifice designed to allow a needle to pass through said wall, the device being characterized in that the first access orifice has a staged structure comprising: a guide portion designed to limit the angular clearance of the needle when the needle is engaged therein, and a flared intake portion that forms a continuation of the guide portion, so as to be able to cause the trajectory of the incoming needle to converge on the guide portion.

Applicant believes that another reference corresponds to U.S. Pat. No. 8,398,577 issued to Daniel R. Burnett on Mar. 19, 2013 for Implantable fluid management device for the removal of excess fluid. However, it differs from the present invention because Burnett teaches a device for removing fluid from a first bodily cavity and for directing that fluid into a second bodily cavity while avoiding risks of infection and excessive dehydration of the first bodily cavity. The device includes an uptake tube having a proximal end in fluid communication with the first bodily cavity and a distal end in fluid communication with a pump, and an outflow tube having a proximal end in fluid communication with the pump and a distal end in fluid communication with the second bodily cavity. The distal end of the uptake tube may be coupled to a reservoir configured to expand upon ingression of fluid into the reservoir and to contract upon removal of fluid due to a negative pressure provided by the pump.

Applicant believes that another reference corresponds to U.S. Pat. No. 8,608,728 issued to Michels, et al. on Dec. 17, 2013 for Delivery system and method. However, it differs from the present invention because Michels, et al. teach a connector and method of connecting for connecting a first and second catheter at an overlap area where the first catheter fits within the second catheter. The connector includes a collar that surrounds a portion of the overlap area and a clamp that applies a radially inward force to the collar and encircles a portion of the overlap area.

Applicant believes that another reference corresponds to U.S. Pat. No. 8,708,979 issued to Honaryar, et al. on Apr. 29, 2014 for Implantable coupling device. However, it differs from the present invention because Honaryar, et al. teach a system for attaching a fluid access port to a patient. The system generally comprises an implantable access port and method for attaching an access port to a patient. In addition, a tube guard, tube shroud, tissue guard, porous coupling member and a prefabricated mesh member may be attached to the access port. For example, the prefabricated mesh may be coupled to the access port to facilitate securing the access port to the tissue of the patient.

Applicant believes that another reference corresponds to U.S. Pat. No. 8,852,160 issued to Schweikert, et al. on Oct. 7, 2014 for Venous access port with molded and/or radiopaque indicia. However, it differs from the present invention because Schweikert, et al. teach a venous access port assembly having a housing base, a flange, and a septum. The housing base defines an interior reservoir. The flange includes integrally molded X-ray discernable indicia identifying that the assembly is rated for power injection. The X-ray discernable indicia may extend through a height of the flange from a top surface to a bottom surface of the flange. According to one aspect, the flange may be formed from X-ray discernable material, and the X-ray discernable indicia may be formed from the X-ray discernable material of the flange, or they may be formed by voids in the X-ray discernable material. According to another aspect, the flange may be formed from a radiotransparent or radiolucent material and applied with a radiopaque agent, and the X-ray discernable indicia may be one or more voids in the radiopaque agent or may be portions of the flange applied with the radiopaque agent.

Applicant believes that another reference corresponds to U.S. Pat. No. 8,852,217 issued to Woodruff, et al. on Oct. 7, 2014 for Implantable injection port with tissue in-growth promoter. However, it differs from the present invention because Woodruff, et al. teach a surgically implantable injection port having a tissue in-growth promoting surface associated with a fluid conduit that is coupled to the injection port. The injection port includes a housing, a fluid reservoir defined in part by the housing, a needle penetrable septum, a fluid conduit in communication with the reservoir, and a tissue in-growth promoting surface coupled to the fluid conduit. The tissue in-growth promoting surface may be provided by surgical mesh wrapped around the conduit or through which the conduit is threaded. The injection port and the fluid conduit may be used as part of a gastric band system or some other type of system.

Applicant believes that another reference corresponds to U.S. Pat. No. 8,858,514 issued to Pierre Sarradon on Oct. 14, 2014 for Internal device for injection and sampling of a liquid inside a living organism. However, it differs from the present invention because Sarradon teaches a device to inject and/or to take a sample, with the aid of a needle, of a liquid inside the organism of a living being, through the skin in a repeated manner. A device intended to be implanted inside a living, human or animal organism, presenting a vascular system and a skin, to exchange a liquid with the vascular system, through the skin and in a repeated manner, using a needle, the aforementioned device including at least a first tubular puncture site, shaped to be able to be perforated numerous times over all its length, the tubular puncture site being linked up in a watertight manner with a flexible link conduit with the vascular system, the tubular puncture site including an watertight flexible tubing, supported by reinforcement constituted by rigid rings, this being shaped to allow the puncture site to lose its shape to follow the body movements of the patient without causing discomfort.

Applicant believes that another reference corresponds to U.S. Pat. No. 8,876,788 issued to Bradley J. Glenn on Nov. 4, 2014 for Stabilized implantable vascular access port. However, it differs from the present invention because Glenn teaches a subcutaneously implantable vascular access port that has two parts including a body and a wing. The body supports a chamber covered by a septum, with a septum held in place over the chamber by a collar. The chamber is coupleable to a vascular structure, such as through tubing extending from the body, for delivery of medical preparations. The body is preferably elongate in form. The wing is configured to be adjustable in width. In one embodiment the wing rotates relative to the body and has an elongate form similar to that of the body. When the wing is rotated it extends laterally from the body and enhances a stability of the body. In another embodiment, the wing is provided as a deformable wing, which can expand laterally out of side openings of a cavern in the body into which the deformable wing is inserted.

Applicant believes that another reference corresponds to U.S. Pat. No. 8,882,728 issued to Harders, et al. on Nov. 11, 2014 for Implantable Injection Port. However, it differs from the present invention because Harders, et al. teach an implantable injection port facilitates filling and/or draining an inflatable portion of a gastric band. The port comprises a movable cap that causes anchor wires to extend from anchor devices in order to implant the injection port in the tissue of a patient. The port comprises a handle that rotates to implant curved anchors into the tissue of a patient. A cap is configured to move towards a base of the port in order to cause the curved anchors to rotate into the tissue of a patient. The cap may also rotate with respect to the base in order to lock the cap and the anchors in position. Further, surfaces of the injection port may be textured to increase adhesiveness to the patient's tissue during installation and to facilitate simpler installation.

Applicant believes that another reference corresponds to U.S. Pat. No. 8,926,573 issued to Smith, et al. on Jan. 6, 2015 for Implantable access port. However, it differs from the present invention because Smith, et al. teach an implantable access port for use in transferring a fluid transdermally between an external fluid storage or dispensing device and a site within a patient's body. The access port includes a base, a bowl-shaped reservoir defined within the base by a smooth surfaced wall, and a septum secured to the base and enclosing the reservoir within the base. The access port also has an outlet passageway defined within the base and extending in communication with a reservoir outlet defined within the reservoir and an external opening defined in the exterior of the base.

Applicant believes that another reference corresponds to U.S. Pat. No. 8,932,271 issued to Hamatake, et al. on Jan. 13, 2015 for Implantable medical devices including septum-based indicators. However, it differs from the present invention because Hamatake, et al. teach an access port for providing subcutaneous access to a patient. The access port includes a septum including palpable identification indicia thereon. In particular, the access port includes a body that defines a fluid cavity and a needle-penetrable septum covering the fluid cavity for providing access thereto. The septum defines an outer periphery. One or more palpation features are included on the septum. The palpation features each include a portion that extends in a radial direction beyond the outer periphery of the septum. The palpation features are therefore disposed relatively farther away from each other, simplifying palpation and identification thereof after the port has been subcutaneously implanted into a patient. The palpation features can be indicative of an attribute of the port, such as its ability to withstand fluid pressures and flow rates associated with power injection.

Applicant believes that another reference corresponds to U.S. Pat. No. 8,974,422 issued to Gill, et al. on Mar. 10, 2015 for Neurological apparatus comprising a percutaneous access device. However, it differs from the present invention because Gill, et al. teach an apparatus for delivering therapeutic agents to the central nervous system of a subject is described. The apparatus comprises at least one intracranial catheter and a percutaneous access device. The percutaneous access device comprises a body having at least one extracorporeal surface and at least one subcutaneous surface, the body defining at least one port for connection to an implanted intracranial catheter. The port is accessible from the extracorporeal surface of the device, but is provided with a seal such as a rubber bung between the lumen of the port and the extracorporeal surface. The percutaneous access device may have more than two ports and a flange.

Applicant believes that another reference corresponds to U.S. Pat. No. 9,033,931 issued to Young, et al. on May 19, 2015 for Subcutaneous vascular access ports having attachment features. However, it differs from the present invention because Young, et al. teach ports for accessing a vessels within a patient include passageways that can guide needles or other access devices directly into the vessels. The ports can be implanted subcutaneously within a patient. Some ports may be used in the creation and use of vascular access buttonholes.

Applicant believes that another reference corresponds to U.S. Pat. No. 9,174,037 issued to Schutz, et al. on Nov. 3, 2015 for Implanted access port. However, it differs from the present invention because Schutz, et al. teach a implantable access port for removal and/or return of fluids to a patient, comprising an internal conduit connectable at its proximal end to the access port and at its distal end to a vascular structure of the patient; an external conduit connectable at its proximal end to the access port and at its distal end to an extracorporeal device; and a transcutaneous coupling member destined to be anchored in a tissue of the patient and comprising a first valve system operable to be in an open or closed configuration; the coupling member further comprises a second valve system removably connectable to the first valve system and operable to be in an open or closed configuration, such as to establish fluid communication between the internal and external conduits when the first and second valve systems are connected and in open configuration.

Applicant believes that another reference corresponds to U.S. Pat. No. 9,295,809 issued to Kevin W. Sheetz on Mar. 29, 2016 for Fixation and protection of an implanted medical device. However, it differs from the present invention because Sheetz teaches a fixation and protective components for use with implantable medical devices, such as access ports and catheter sidewalls. A protective sleeve is employed about a catheter so as to distribute compressive loads and ensure patency of the catheter lumen, even in areas prone to pinch-off. A catheter assembly thus comprises an elongate catheter tube that defines at least one lumen. A protective mesh sleeve is disposed about an external portion of the catheter tube so as to cover at least a portion of the longitudinal length of the catheter tube. The protective sleeve is configured to distribute a compressive load on the catheter tube so as to ensure patency of the at least one lumen of the catheter tube.

Applicant believes that another reference corresponds to U.S. Pat. No. 9,415,187 issued to Charles W. Agnew on Aug. 16, 2016 for Dialysis catheter. However, it differs from the present invention because Agnew teaches a catheter assembly used for extracorporeal treatment, such as dialysis, of blood or other body fluid, includes an outer and inner catheter in a coaxial relationship. The catheter assembly has fluid path by a passageway defined between the catheter sidewalls and a distal end of the outer catheter, and another fluid path through a lumen and a distal end of the inner catheter. A sealing member is coupled to one of the catheter sidewalls. The member in a first position is configured to permit the distal ends of the catheter to transport fluid, while in a second position the member is configured to inhibit at least one of the distal ends from transporting fluid. The sealing member may include a flared portion for enhance sealing. The sealing member may also have a portion extending outward from the catheter to position the distal ends away from vessel contact.

Applicant believes that another reference corresponds to U.S. Pat. No. RE44639 issued to Rafael P. Squitieri on Dec. 10, 2013 for Hemodialysis and vascular access system. However, it differs from the present invention because Squitieri teaches a hemodialysis and vascular access system comprises a subcutaneous composite PTFE silastic arteriovenous fistula having an indwelling silastic venous end which is inserted percutaneously into a vein and a PTFE arterial end, which is anastomosed to an artery. Access to a blood stream within the system is gained by direct puncture of needle(s) into a needle-receiving site having a tubular passage within a metal or plastic frame and a silicone upper surface through which needle(s) are inserted. Percutaneous access to a blood stream may be gained by placing needles directly into the system. An arterialized indwelling venous catheter where blood flows from an artery through a tube and a port into an arterial reservoir and is returned to a vein via a port and a venous outlet tube distinct and distant from the area where the blood from the artery enters the arterial reservoir. The site where blood is returned to the vein is not directly fixed to the venous wall but is free floating within the vein. This system provides a hemodialysis and venous access graft.

Other patents describing the closest subject matter provide for a number of more or less complicated features that fail to solve the problem in an efficient and economical way. None of these patents suggest the novel features of the present invention.

SUMMARY OF THE INVENTION

The present invention is an accessing assembly for hemodialysis administration, comprising an intravascular tube assembly, a conduit assembly, first and second catheter sleeve assemblies, and first and second catheter assemblies.

The intravascular tube assembly comprises an intravascular tube, a subcutaneous cuff, a tube end and a ring with a hole. The conduit assembly comprises first and second conduits having respective first and second conduit threading. The conduit assembly further comprises first and second ends having respective first and second diaphragms. The first and second conduits are joined within the intravascular tube and extend together therefrom until a bifurcation whereby the first and second conduits separate.

The first and second catheter sleeve assemblies comprise first and second collapsible sidewalls, first and second ends, and first and second joining ends respectively. The first and second collapsible sidewalls define respective first and second cavities and first and second couplers are defined within the first and second cavities respectively, extending from the first and second joining ends respectively. The first and second couplers comprise respective first and second external threads and respective first and second internal threads.

The first and second catheter assemblies comprise first and second catheter sidewalls respectively, which comprise respective first and second inlet/outlet ends and respective first and second internal ends. The first and second catheter assemblies further comprise respective first and second fasteners having respective first and second fastener internal threading. The first and second catheter assemblies further comprise respective first and second catheter external threading. The first and second catheter sidewalls comprise a plurality of holes extending from first and second internal ends respectively.

The intravascular tube is implanted within a vascular structure. The ring is surgically fixed onto a patient through the hole. The first and second couplers are positioned onto respective first and second conduits, whereby respective first and second internal threads are threaded onto respective first and second conduit threading. The first and second catheter sidewalls are positioned inside to respective first and second collapsible sidewalls. The first and second collapsible sidewalls are collapsed until respective first and second fasteners are threaded onto respective first and second external threads of first and second couplers. The first and second catheter sidewalls extend inside of respective first and second conduits and both extend from the tube end a predetermined length, whereby the plurality of holes are exposed from the intravascular tube.

It is therefore one of the main objects of the present invention to provide an accessing assembly for hemodialysis administration.

It is another object of this invention to provide an accessing assembly for hemodialysis administration, which has a single intravascular tube.

It is another object of this invention to provide an accessing assembly having a catheter sleeve assembly, which has collapsible sidewalls.

It is another object of this invention to provide an accessing assembly that can be also used for infusion of chemotherapy, long-term antibiotic therapy or any other long treatment.

It is another object of this invention to provide an accessing assembly, which is of a durable and reliable construction.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Referring now to the drawings, the present invention is an accessing assembly for hemodialysis administration, and is generally referred to with numeral 10. It can be observed that it basically includes intravascular tube assembly 20, conduit assembly 40, first and second catheter sleeve assemblies 60, and first and second catheter assemblies 90.

Figure 1:
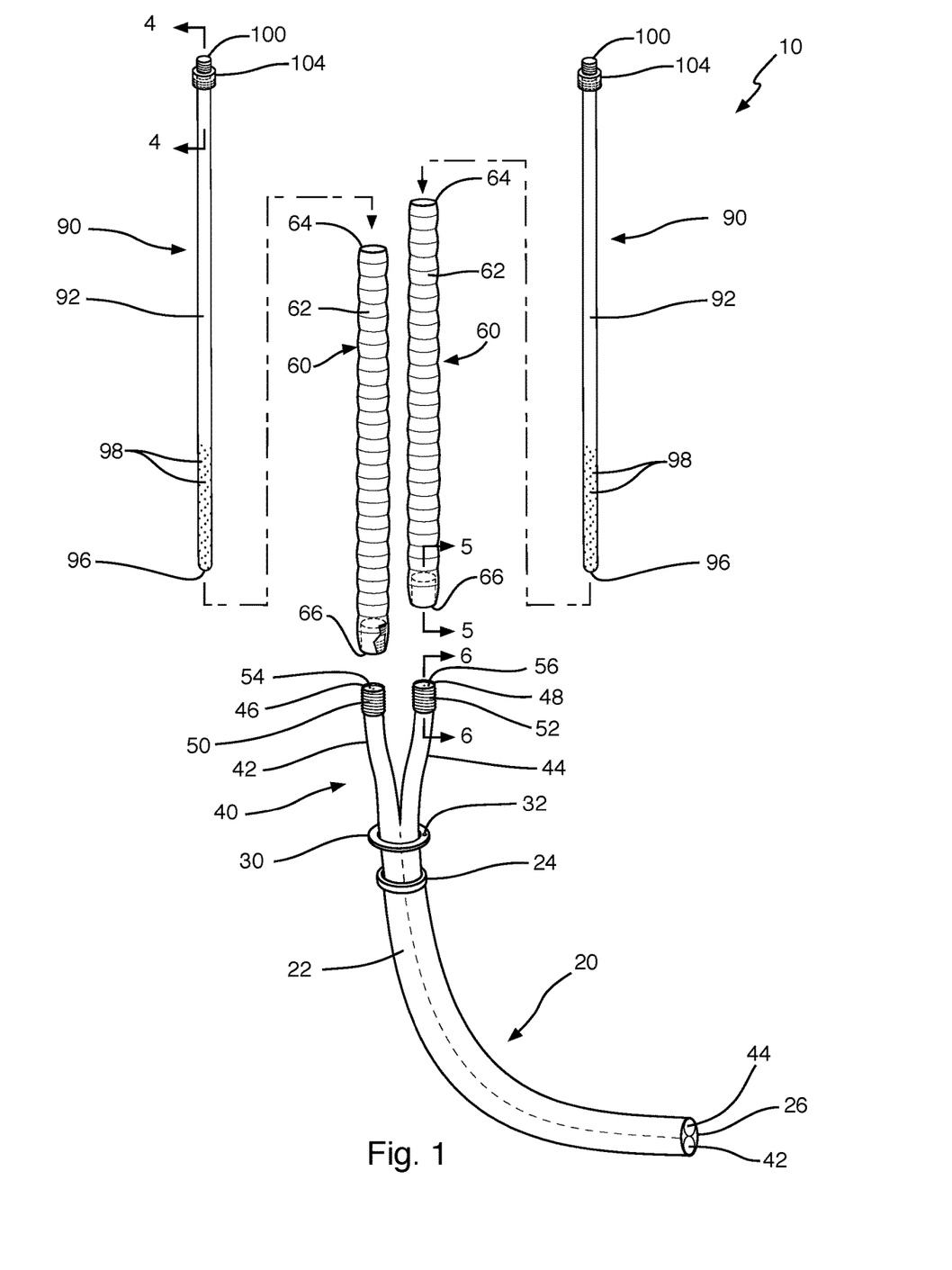
FIG. 1 is a first isometric view of the present invention.
Figure 2:
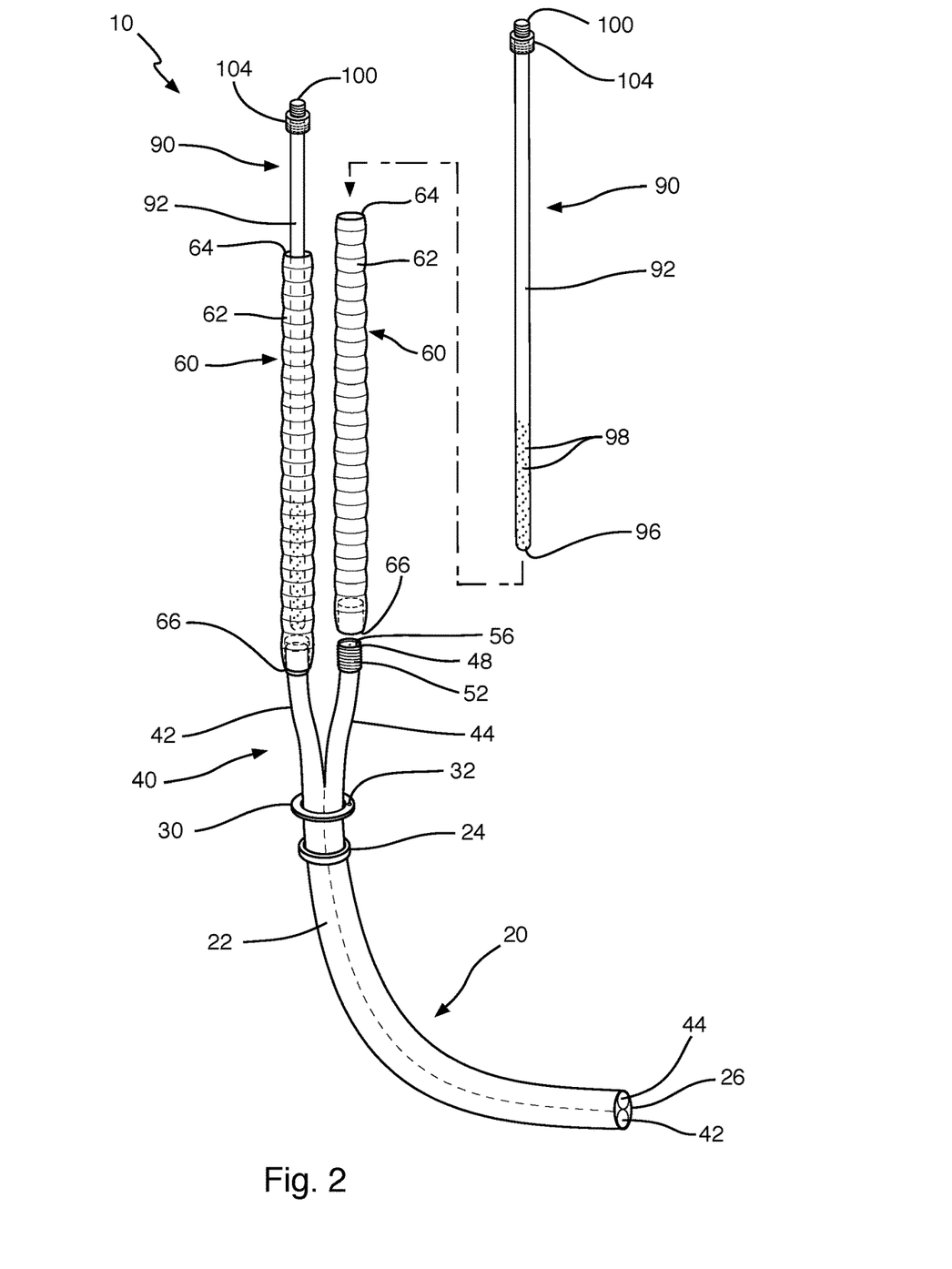
FIG. 2 is a second isometric view of the present invention with a first catheter assembly positioned inside a first catheter sleeve assembly that is coupled to a first conduit.

As seen in FIGS. 1 and 2, intravascular tube assembly 20 comprises intravascular tube 22, subcutaneous cuff 24, tube end 26, and ring 30 with hole 32.

Intravascular tube 22 is implanted within a vascular structure of a patient, not seen, wherein intravascular tube 22 is a vascular access device for the passage of large quantities of fluids including blood through an extra-corporeal circuit during a hemodialysis procedure of the patient. Subcutaneous cuff 24 is made of a porous material that allows an ingrowth of tissue to adhere subcutaneous cuff 24 in the subcutaneous tissue of the patient, not seen. In a preferred embodiment, ring 30 is surgically fixed onto skin of a patient with sutures through hole 32. This secures intravascular tube assembly 20 to the body of the patient.

Conduit assembly 40 comprises first conduit 42 having conduit threading 50, and second conduit 44 having conduit threading 52. Conduit assembly 40 further comprises first end 46 having diaphragm 54, and second end 48 having diaphragm 56.

First and second conduits 42 and 44 are positioned within intravascular tube 22 to allow access of first and second catheter assemblies 90 into the vascular structure. In a preferred embodiment, first and second catheter assemblies 90 are disposable after each use.

First and second conduits 42 and 44 are joined within intravascular tube 22 and extend together therefrom until a bifurcation, whereby first conduit 42 and second conduit 44 separate. In addition, first and second conduits 42 and 44 protrude from the patient's body, whereby they extend from ring 30. Diaphragms 54 and 56 keep respective first and second ends 46 and 48 relatively closed when respective catheter assemblies 90 are removed from respective conduits 42 and 44.

First and second sleeve assemblies 60 each comprise collapsible sidewall 62 having end 64 and joining end 66. First and second catheter assemblies 90 each comprise sidewall 92 with inlet/outlet end 100. Sidewalls 92 each comprise respective internal ends 96, and a plurality of holes 98 extending therefrom that do not reach inlet/outlet ends 100. Plurality of holes 98 are small perforations which allow fluids, medications, and/or blood to be delivered or returned to a patient during the hemodialysis procedure. Inlet/outlet ends 100 serve as inlet or outlet ports for the fluids, medications, and/or blood to travel through during the hemodialysis procedure. When first inlet/outlet end 100 acts as an inlet port, second inlet/outlet end 100 acts as an outlet port, and vice versa.

Figure 3:
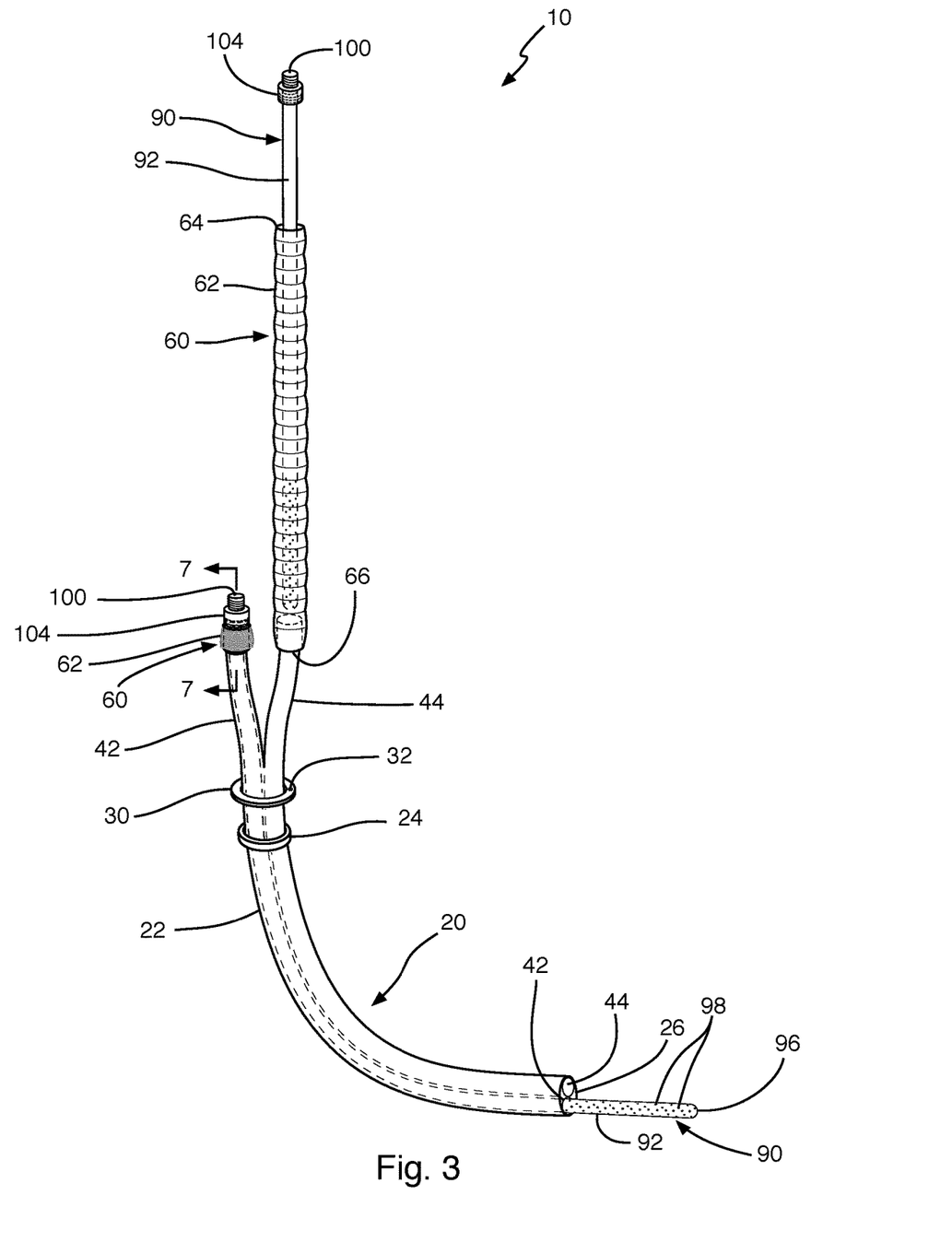
FIG. 3 is a third isometric view of the present invention with the first catheter sleeve assembly collapsed and the first catheter assembly extending through the first conduit, and a second catheter assembly positioned inside a second catheter sleeve assembly that is coupled to a second conduit.
Figure 7:
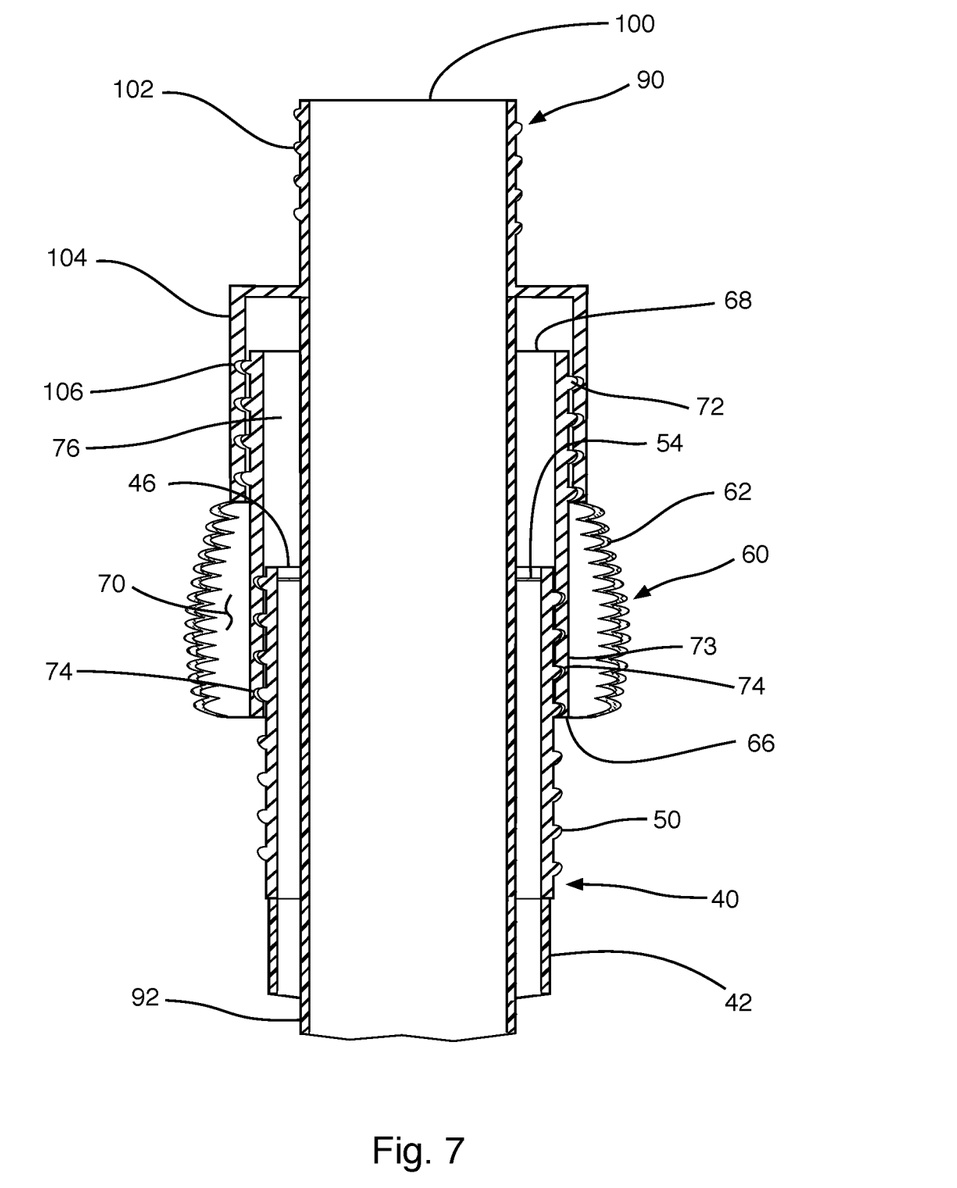
FIG. 7 is a cut view taken along the lines 7-7 as seen in FIG. 3.

As seen in FIG. 3, first and second catheter assemblies 90 are positioned inside first and second catheter sleeve assemblies 60, whereby respective catheter sidewalls 92 are positioned inside respective collapsible sidewalls 62. Collapsible sidewalls 62 collapse in order for fasteners 104 to couple onto respective couplers 76 as seen in FIG. 7. Collapsible sidewalls 62 are made of an appropriate material to allow collapsible sidewalls 62 to collapse.

In the illustrated embodiment, first catheter sidewall 92 passes through conduit 42 and extends from tube end 26 a predetermined length, whereby first plurality of holes 98 are exposed from intravascular tube 22 to enter the vascular structure, not seen. Although not illustrated, it is noted that in use, second catheter sidewall 92 passes through respective conduit 44 to also extend from tube end 26 a predetermined length, and second plurality of holes 98 are also exposed from intravascular tube 22 to enter the vascular structure.

Catheter assemblies 90 are made of a biologically inert polymeric silicone substance, commonly used for temporary implants in tissue. In a preferred embodiment, catheter assemblies 90 may be made of a flexible and inert silicone elastomer. Such a flexible and inert silicone elastomer as an example it under trademark SILASTIC®. Catheter assemblies 90 may comprise markings that allow a technician to know when to stop to flush with heparin, which is a blood thinner.

Figure 4:
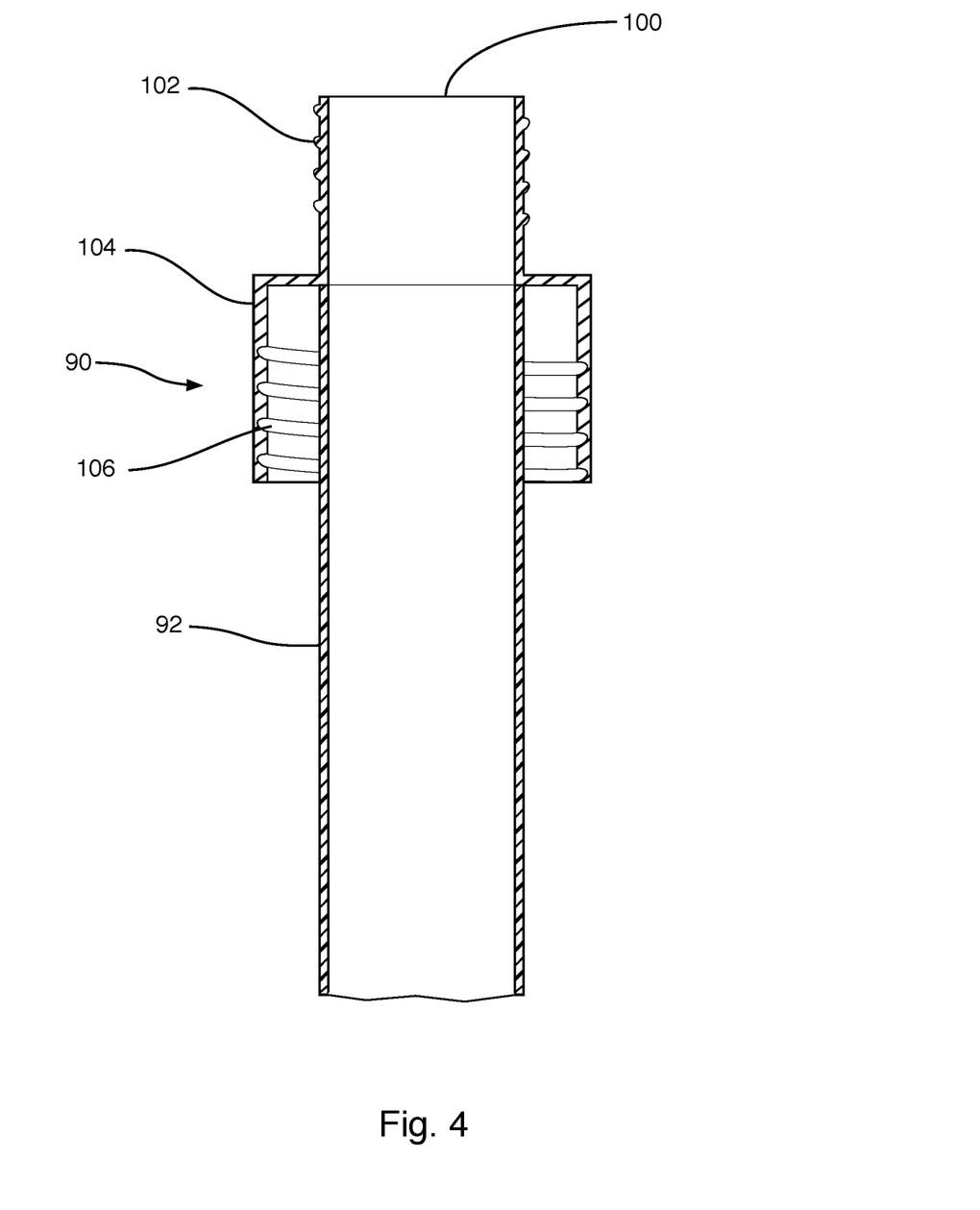
FIG. 4 is a cut view of a section of the first catheter assembly taken along the lines 4-4 as seen in FIG. 1.

As seen in FIG. 4, catheter assembly 90 comprises fastener 104, which has fastener internal threading 106. Fastener internal threading 106 is inside fastener 104 to thread fastener 104 to external threads 72 of coupler 76 as seen in FIG. 7. Catheter assembly 90 further comprises catheter external threading 102. Catheter external threading 102 extends from fastener 104 to inlet/outlet end 100, to couple an external tubing for connection with the hemodialysis machine, not seen.

Figure 5:
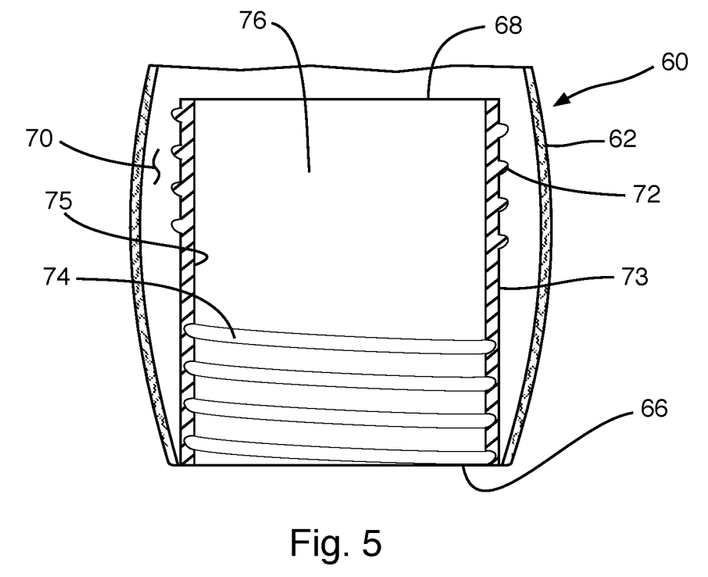
FIG. 5 is a cut view of a section of the second catheter sleeve assembly taken along the lines 5-5 as seen in FIG. 1.

As seen in FIG. 5, collapsible sidewall 62 of catheter sleeve assembly 60 defines cavity 70. Coupler 76 is defined within cavity 70 extending from joining end 66. Couplers 76 comprise coupler end 68, external threads 72, external face 73, internal threads 74 and internal face 75. External threads 72 are positioned on external face 73 close to coupler end 68, and internal threads 74 are positioned on internal face 75 close to joining end 66.

Figure 6:
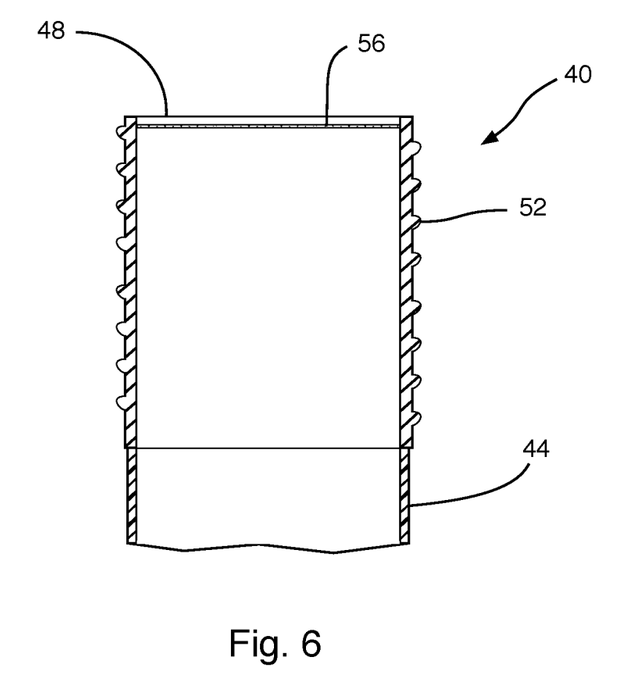
FIG. 6 is a cut view of a section of the second conduit taken along the lines 6-6 as seen in FIG. 1.

As seen in FIG. 6, conduit assembly 40 comprises conduit 44 having end 48 and conduit threading 52. Conduit threading 52 receives respective internal threads 74 of couplers 76, as seen in FIG. 7.

As seen in FIG. 7, first catheter sidewall 92 passes through conduit 42. First collapsible sidewall 62 collapses until first fastener 104 couples onto first coupler 76, whereby first fastener internal threading 106 is threaded onto first external threads 72. First coupler 76 couples onto respective conduit 42, whereby respective internal threads 74 are threaded onto conduit threading 50. It is noted that when second catheter sidewall 92 passes through conduit 44, second collapsible sidewall 62 also collapses until second fastener 104 couples onto second coupler 76, whereby second fastener internal threading 106 is threaded onto second external threads 72. Second coupler 76 couples onto respective conduit 44, whereby respective internal threads 74 are threaded onto conduit threading 52.

In other embodiments, present invention 10 provides an accessing assembly that may be also used for infusion of chemotherapy, long-term antibiotic therapy, delivery of fluids, and/or any other treatments.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An accessing assembly for hemodialysis administration, comprising:
    A) an intravascular tube assembly comprising comprises an intravascular tube, a subcutaneous cuff, a tube end and a ring with a hole;
    B) a conduit assembly comprising first and second conduits having respective first and second conduit threading;
    C) first and second catheter sleeve assemblies comprise first and second collapsible sidewalls, first and second ends, and first and second joining ends respectively, said first and second collapsible sidewalls define respective first and second cavities; and
    D) first and second catheter assemblies.

2. The accessing assembly for hemodialysis administration set forth in claim 1, further characterized in that said conduit assembly further comprises first and second ends having respective first and second diaphragms.

3. The accessing assembly for hemodialysis administration set forth in claim 1, further characterized in that said first and second conduits are joined within said intravascular tube and extend together therefrom until a bifurcation whereby said first and second conduits separate.

4. The accessing assembly for hemodialysis administration set forth in claim 1, further characterized in that first and second couplers are defined within said first and second cavities, extending from said first and second joining ends respectively.

5. The accessing assembly for hemodialysis administration set forth in claim 4, further characterized in that said first and second couplers comprise respective first and second external threads and respective first and second internal threads.

6. The accessing assembly for hemodialysis administration set forth in claim 5, further characterized in that said first and second couplers are positioned onto respective said first and second conduits, whereby respective said first and second internal threads are threaded onto respective said first and second conduit threading.

7. The accessing assembly for hemodialysis administration set forth in claim 1, further characterized in that said first and second catheter assemblies comprise first and second catheter sidewalls respectively.

8. The accessing assembly for hemodialysis administration set forth in claim 7, further characterized in that said first and second catheter sidewalls comprise respective first and second inlet/outlet ends and respective first and second internal ends.

9. The accessing assembly for hemodialysis administration set forth in claim 7, further characterized in that said first and second catheter sidewalls comprise a plurality of holes extending from said first and second internal ends respectively.

10. The accessing assembly for hemodialysis administration set forth in claim 9, further characterized in that said first and second catheter sidewalls extend inside of respective first and second conduits and both extend from said tube end a predetermined length, whereby said plurality of holes are exposed from said intravascular tube.

11. The accessing assembly for hemodialysis administration set forth in claim 7, further characterized in that said first and second catheter sidewalls are positioned inside to respective said first and second collapsible sidewalls.

12. The accessing assembly for hemodialysis administration set forth in claim 1, further characterized in that said first and second catheter assemblies further comprise respective first and second fasteners.

13. The accessing assembly for hemodialysis administration set forth in claim 12, further characterized in that said first and second collapsible sidewalls are collapsed until respective said first and second fasteners are threaded onto respective said first and second external threads of said first and second couplers.

14. The accessing assembly for hemodialysis administration set forth in claim 1, further characterized in that said first and second catheter assemblies further comprise respective first and second fastener internal threading and respective first and second catheter external threading.

15. The accessing assembly for hemodialysis administration set forth in claim 1, further characterized in that said intravascular tube is implanted within a vascular structure.

16. The accessing assembly for hemodialysis administration set forth in claim 1, further characterized in that said ring is surgically fixed onto a patient through said hole.

* * * * *